(12) United States Patent
Scalzi et al.

(10) Patent No.: US 9,637,731 B2
(45) Date of Patent: *May 2, 2017

(54) HEAVY METAL STABILIZATION AND METHANE INHIBITION DURING INDUCED OR NATURALLY OCCURRING REDUCING CONDITIONS IN CONTAMINATED MEDIA

(71) Applicant: Innovative Environmental Technologies, Inc., Pipersville, PA (US)

(72) Inventors: Michael Scalzi, Doylestown, PA (US); Antonis Karachalios, North Wales, PA (US)

(73) Assignee: Innovative Environmental Technologies, Inc., Pipersville, PA (US)

( * ) Notice: Subject to any disclaimer, the term of this patent is extended or adjusted under 35 U.S.C. 154(b) by 15 days.

This patent is subject to a terminal disclaimer.

(21) Appl. No.: 14/532,689

(22) Filed: Nov. 4, 2014

(65) Prior Publication Data

US 2015/0183670 A1 Jul. 2, 2015

Related U.S. Application Data

(63) Continuation-in-part of application No. 13/785,840, filed on Mar. 5, 2013, now Pat. No. 9,221,699.

(51) Int. Cl.
*C02F 3/02* (2006.01)
*C02F 9/00* (2006.01)
(Continued)

(52) U.S. Cl.
CPC ............... *C12N 9/99* (2013.01); *B09C 1/08* (2013.01); *B09C 1/10* (2013.01); *C02F 3/282* (2013.01);
(Continued)

(58) Field of Classification Search
CPC ...... C02F 11/04; C02F 3/342; C02F 2101/20; C02F 2103/06; C02F 101/32; C02F 101/36; C02F 103/06; B01D 1/04; B09C 1/08
(Continued)

(56) References Cited

U.S. PATENT DOCUMENTS 5,116,415 A * 5/1992 Rinehart ............... B01D 15/00
423/25
5,648,258 A 7/1997 Odom
(Continued)

FOREIGN PATENT DOCUMENTS

CN 1908156 2/2007

OTHER PUBLICATIONS

Siriwongrungson, "Homoacetogenesis as the Alternative Pathway for H2 Sink During Thermophilic Anaerobic Degradation of Butyrate Under Suppressed Methanogensis", Water Res., Oct. 2007 41(18): 4204-1, Epub May 25, 2007.
(Continued)

*Primary Examiner* — Ana Fortuna
(74) *Attorney, Agent, or Firm* — Douglas J. Ryder; Ryder, Lu, Mazzeo & Konieczny LLC (57) ABSTRACT

A method for inhibiting methane production in naturally occurring or induced reducing conditions, thus subsequently resulting into inhibition of the biomethylation process of the heavy metals is disclosed. The disclosed inhibiting composition blocks 3-hydroxy-3-ethylglutaryl coenzyme A (HMG-CoA) reductase, and 8-hydroxy-5-deazaflavin (coenzyme $F_{420}$) in the methane production pathway, due to the presence of lovastatin in the red yeast rice. As a result the methanogens are unable to produce enough quantities of methane that will result to the production of methylmetal (loids), which are usually volatile and more toxic than their
(Continued)

inorganic counterparts due to increased water solubility and hydrophobicity.

20 Claims, 5 Drawing Sheets

(51) Int. Cl.
| | |
|---|---|
| C12N 9/99 | (2006.01) |
| B09C 1/08 | (2006.01) |
| C02F 3/34 | (2006.01) |
| B09C 1/10 | (2006.01) |
| C02F 3/28 | (2006.01) |
| C02F 103/06 | (2006.01) |
| C02F 101/20 | (2006.01) |
| C02F 101/32 | (2006.01) |
| C02F 101/36 | (2006.01) |

(52) U.S. Cl.
CPC .............. *C02F 3/342* (2013.01); *C02F 3/344* (2013.01); *B09C 2101/00* (2013.01); *C02F 2101/20* (2013.01); *C02F 2101/322* (2013.01); *C02F 2101/36* (2013.01); *C02F 2103/06* (2013.01); *C02F 2305/06* (2013.01); *Y02E 50/343* (2013.01)

(58) Field of Classification Search
USPC ....................................................... 210/606
See application file for complete search history.

(56) References Cited

U.S. PATENT DOCUMENTS

| | | | |
|---|---|---|---|
| 5,788,857 | A | 8/1998 | Yang et al. |
| 5,985,907 | A | 11/1999 | Wolin et al. |
| 6,150,157 | A | 11/2000 | Keasling et al. |
| 6,251,836 | B1 | 6/2001 | Duncum et al. |
| 6,398,960 | B1 | 6/2002 | Borden et al. |
| 6,436,877 | B1 | 8/2002 | Duncum et al. |
| 6,596,911 | B2 | 7/2003 | Przybylinski et al. |
| 9,126,244 | B2* | 9/2015 | Scalzi ....................... B09C 1/10 |
| 9,221,699 | B2* | 12/2015 | Scalzi ....................... C02F 3/342 |
| 2008/0299187 | A1* | 12/2008 | Opheim ............... A61K 9/4875 424/452 |
| 2009/0308816 | A1* | 12/2009 | Horst ........................ C02F 1/52 210/719 |
| 2010/0184624 | A1 | 7/2010 | Samuel et al. |
| 2010/0239603 | A1 | 9/2010 | Wang et al. |
| 2010/0314312 | A1 | 12/2010 | Baseeth et al. |
| 2011/0008876 | A1 | 1/2011 | Scalzi et al. |
| 2011/0280852 | A1 | 11/2011 | Miller |
| 2012/0178147 | A1 | 7/2012 | Krajmalnik-Brown et al. |
| 2012/0199492 | A1* | 8/2012 | Jin ............................. C25B 3/04 205/413 |
| 2013/0189297 | A1* | 7/2013 | Richards ............... A23L 1/3002 424/195.15 |
| 2014/0128289 | A1* | 5/2014 | Gordon ............ G01N 33/56911 506/16 |
| 2014/0200204 | A1* | 7/2014 | Gross ..................... A61K 45/06 514/184 |
| 2014/0322798 | A1* | 10/2014 | Scalzi ....................... B09C 1/10 435/252.1 |
| 2015/0183670 | A1* | 7/2015 | Scalzi ....................... C12N 9/99 435/184 |
| 2016/0076057 | A1* | 3/2016 | Scalzi ..................... C12P 5/023 435/184 |

OTHER PUBLICATIONS

Rasche et al., "Mechanism for the Enzymatic Formation of 4-(beta-D-ribofuranosyl)aminobenzene 5'-phosphate During the Biosynthesis of Methanopterin", Biochemistry, 1998 Aug. 2011, 37(32): 11343-11351.

Nagar-Anthal, "The Pterin Lumazine Inhibits Growth of Methanogens and Methane Formation", Archives of Microbiology, Aug. 1996, vol. 166, Issue 2, pp. 136-140.

Miller-Wolin, "Control of Rumen Methanogenesis by Inhibiting the Growth and Activity of Methanogens with hydroxymtheylglutaryl-SCoa Inhibitors", International Congress Series, Jul. 2008, vol. 1293, pp. 131-137.

Wust, "Trophic Links Between Fermenters and Methanogens in a Moderately Acidic Fen Soil", Environ Microbiol., Jun. 2009, 11 (6): 1395-1409. doi:10.1111/j. 1462-2920.2009.01867.x.

Liu et al., "Metabolic Phylogenetic and Ecological Diversity of the Methanogenic Archaea", Annals of the New York Academy of Sciences, 1125: 171-189.

Conrad et al., "Phosphate Inhibits Acetotrophic Methanogensis on Rice Roots", Appl. Environ. Microbiol., 2000, 66(2):828.

Dumitru et al., "Mechanism of 4-(Beta-D-Ribofuranosyl)aminobenzene 5-Phosphate Synthase, a Key Enzyme in the Methanopterin Biosynthetic Pathway", The Journal of Biological Chemistry. 2004, vol. 279, No. 38, pp. 39389-39395.

Dumitru et al., "Targeting Methanopterin Biosynthesis to Inhibit Methanogensis", Appl. Environ. Microbiol., Dec. 2003. pp. 7236-7241.

Ferry, "Biochemistry of Methanogensis", Critical Reviews in Biochemistry and Molecular Biology, 1992, 27(6): 473-503.

Ferry, ;Methanogensis Biochemistry, Encyclopedia of Life Sciences, 2002 MacMillan Publishers.

Liu et al., "Chemical Inhibitors of Methanogensis and Putative Applications", Appl. Microbiol. Biotechnol. 2011, 89:1333-1340.

Miller et al., "Inhibition of Growth Methane-Producing Bacteria of the Ruminant Forestomach by Hydroxymethyglutaryl-SCoA Reducatase Inhibitors", 2001, J. Dairy Sc.. 84: 1445-1448.

Reynolds et al., "Evaluation and Improvement of Methodsfor Coenzyme F420 Analysis in Anaerobic Sludges", Journal of Microbiological Methods, 7 (1987) 115-130.

Sharma et al., "Structure Modeling and Inhibitor Prediction of NADP Oxidoreductase Enzyme from Methanobrevibacter Smithil", 2011, Biomedical Informatics.

Zinder et al., "Selective Inhibition by 2-Bromoethanesulfonate of Methanogensis from Acetate in a Thermophilic Anaerobic Digestor", Appl. Environ. Microbiol., Jun. 1984, pp. 1343-1345.

Bouwer et al., "Transformationsof 1- and 2-Carbon Halogenated Aliphatic Organic Compounds Under Methanogenic Conditions", Appl. Environ. Microbiol., Apr. 1983, pp. 1286-1294.

Challenger, "Biological Methylation," Chem. Rev., 1945, 36(3), 315-61.

European Patent Office, Extended European Search Report, Supplementary Search Report, and Search Opinion, App. 14770315.1 (PCT/US2014036632), mailed Feb. 10, 2017, 6 pages.

Zu Bo, et al., "Biophysical and Biochemical Characteristics of Methanogenic Organism," Environmental Science & Technology, vol. 31, No. 3, pp. 5-7 and 51, translation of Abstract only submitted.

* cited by examiner

HEAVY METAL STABILIZATION AND METHANE INHIBITION DURING INDUCED OR NATURALLY OCCURRING REDUCING CONDITIONS IN CONTAMINATED MEDIA

CROSS REFERENCE TO RELATED PATENT APPLICATIONS

This patent application is a continuation-in-part of patent application Ser. No. 13/785,840 entitled "Inhibition of Methane Production During Anaerobic Reductive Dechlorination" and filed Mar. 5, 2013, now U.S. Pat. No. 9,221,699 by the same inventors, priority of which is hereby claimed.

FIELD OF THE DISCLOSURE

The disclosed method relates to the use of red yeast rice extract to inhibit methane production and as a result address the heavy metal contamination via solidification and stabilization processes. The present invention utilizes, the statin containing, red yeast rice extract, to target the methanogenic enzyme and coenzyme systems, thus limiting their effectiveness in producing methane and subsequently preventing the biomethylation process of the heavy metals to take place.

BACKGROUND

Microorganisms play an essential role in the recycling of various elements such as the well-established cycles of carbon, nitrogen and sulfur. Moreover they are critical in the biochemical cycles of heavy metals that also occur in the aquatic and terrestrial environment.

Trace metals constitute a significant class of groundwater contaminants, originating from mining effluents, industrial wastewater, landfill leachate, agricultural wastes and fertilizers, and fossil fuels. Based on the chemical properties of dissolved species trace metals can be divided into two distinctive groups: i) reducible metals and metalloids, which are present in natural waters as anions and oxyanions (e.g.; Cr, As, Se, Mo, U), and ii) metal cations, which occur in aqueous environment as divalent cations (e.g.; Cu, Zn, Cd, Pb, Hg, Ni). Depending on their aqueous form, the mobility of trace metals in groundwater is affected by various chemical reactions, including dissolution-precipitation, oxidation-reduction, adsorption-desorption and complexation. Naturally occurring reducing conditions as well as In Situ Chemical Reduction (ISCR) approaches to address the contamination in the subsurface tend to create the phenomenon of biomethylation of the heavy metals. The ISCR remedial technique that was developed over a decade ago uses an array of synergistic interactions between various biotic (e.g., microbial fermentation of organic carbon sources) and abiotic processes (e.g., zero-valent iron [ZVI] chemistry) to encourage dehalogenation of organic compounds as well as reductive precipitation of various heavy metals. Despite the effectiveness of the method, ISCR processes are often confronted by an inability to meet stringent regulatory requirements. One likely explanation for this phenomenon is that, with the possible exception of lead, almost all Group IV, V and VI elements can be biomethylated. The methylmetal (loids) created are usually volatile and more toxic than their inorganic counterparts due to increased water solubility and hydrophobicity.

Microbes have evolved diverse strategies to overcome the toxic effects of metals and metalloids, utilizing accumulation, resistance or, more interestingly, by reducing their bio-availability or toxicity through biomethylation and transformation. The elevated concentrations of waterborne heavy metals have been recognized as an environmental problem in aquatic ecosystems throughout the world. Some of these heavy metals reach the groundwater and others accumulate in seafood or in plants and represent a major toxic source for humans. Some of them cause deformation of birds and sea animals in addition to some diseases in humans.

The synthesis and transfer of methyl groups is an important and widely distributed metabolic process. The following natural products containing one or more methyl groups attached to nitrogen atoms were discovered early in the 19th century: creatine, creatinine, choline, and trimethylamine. Another compound, trimethylglycine ([trimethylammonio] acetate), originally named lycine (from *Lycium barbarum*) was later renamed betaine (from *Beta vulgaris*). This discovery contributed the term "betaine" to chemical nomenclature to describe zwitterionic types, for instance: $(CH_3)nX^+$—$CH2$-$COO^-$ (if X=N, n=3; if X=S, n=2).

The first observation of a biological methylation came when His, with an interest in the detoxification of aromatic compounds, administered pyridine to a dog. N-Methylpyridine was excreted in the urine. Similar examples of the methylation of aromatic compounds were the conversion, xanthine→methylxanthine in rabbits, and nicotinic acid→trigonelline in dogs.

The role for methionine, a methylated sulfur compound, was also slowly recognized, and S-adenosylmethionine (SAM) was identified as the product of the enzymatic activation of methionine in transmethylation reactions. The role of SAM as the methyl donor in hundreds of methylation reactions is now well established. The mechanism for the de novo biosynthesis of methyl groups has also been determined.

The carbon (C), oxygen (O), nitrogen (N) and sulfur (S) atoms of organic compounds frequently function as methyl group acceptors in primary and secondary metabolic processes. Metalloids specifically tend to be used as methyl group acceptors with a major emphasis on the production of volatile compounds by microorganisms. The term "biomethylation" describes the formation of both volatile and nonvolatile methylated compounds of metals and metalloids.

Biomethylation and hydride generation of group 15 and 16 metals and metalloids (As, Se, Sb, Te, and Bi) by microorganisms are widespread phenomena in anaerobic habitats including landfills, sewage sludge fermentation, alluvial soils, and, as recently shown, the gut of mice and humans.

Microorganisms are primarily responsible for the biosynthesis of organo-metals, and the activity of methanogens is a main source of their production. As Table 1 shows a large number of methanogens have been shown to methylate a variety of metals.

TABLE 1

Volatile Methylmetal(loids) produced by Growing Cultures of Methanogens (Archaea)

| | Metal/metalloid | | | | | Reference |
|---|---|---|---|---|---|---|
| | As | Bi | Se | Te | Sb | |
| *Methanobacterium formicicum* | $AsH_3, CH_3AsH_2$, $(CH_3)_2AsH$, $(CH_3)_3As, X$ | $BiH_3, CH_3BiH_2$, $(CH_3)_2BiH$, $(CH_3)_3Bi$ | $(CH_3)_2Se$, $(CH_3)_2Se_2$ | $(CH_3)_2Te$ | $SbH_3CH_3SbH_2$, $(CH_3)_3SbH$, $(CH_3)_3Sb$ | Michalke et al., 2000 |
| *Methanobrevibacter smithii* | $CH_3AsH_2$, $(CH_3)_2AsH$, $(CH_3)_2As$ | $CH_3BiH_2$, $(CH_3)_2BiH$, $(CH_3)_3Bi$ | $(CH_3)_2Se$, $(CH_3)_2SeS$, $(CH_3)_2Se, X$ | $(CH_3)_2Te$ | $(CH_3)_3Sb$ | This study |
| *Methanococcus vanielli* | $CH_3AsH_2$, $(CH_3)_2AsH$, $(CH_3)_3As, X$ | $CH_3BiH_2$, $(CH_3)_3Bi$ | $(CH_3)_2Se$, $(CH_3)_2SeS$ | $(CH_3)_2Te$ | $(CH_3)_3Sb$ | This study |
| *Methanolacinia paynteri* | n.d. | $(CH_3)_2BiH$, $(CH_3)_3Bi$ | $(CH_3)_2Se$, $(CH_3)_2SeS$, $(CH_3)_2Se_2, X$ | $(CH_3)_2Te$ | $(CH_3)_3Sb$ | This study |
| *Methanolobus tindarius* | n.d. | $(CH_3)_3Bi$ | $(CH_3)_2Se, X$ | $(CH_3)_2Te$ | $CH_3SbH_2, (CH_3)_3Sb$ | This study |
| *Methanoplanus limicola* | $(CH_3)_3As$ | $(CH_3)_3Bi$ | $(CH_3)_2Se$, $(CH_3)_2SeS$, $(CH_3)_2Se_2, X$ | $(CH_3)_2Te, X$ | $(CH_3)_3Sb$ | This study |
| *Methanosarcina barkeri* | $AsH_3, X$ | $(CH_3)_3Bi*$ | $(CH_3)_2Se$, $(CH_3)_2Se_2$ | n.d. | $(CH_3)_3Sb$ | Michalke et al., 2000 |
| *Methanosarcina mazei* | $(CH_3)_3As$ | $(CH_3)_3Bi$ | $(CH_3)_2Se$, $(CH_3)_2Se$, | $(CH_3)_2Te$ | $(CH_3)_3Sb$ | This study |
| *Methanosphaera stadtmanae* | $(CH_3)_2AsH$, $(CH_3)_3As$ | $CH_3BiH_2$, $(CH_3)_2BiH$, $(CH_3)_3Bi$ | $(CH_3)_2Se$, $(CH_3)_2SeS$, $(CH_3)_2Se_2, X$ | $(CH_3)_2Te$ | $(CH_3)_3Sb$ | This study |
| *Methanothermobacter thermautotrophicus* | $AsH_3$ | n.d. | n.d. | n.d. | $(CH_3)_3Sb$ | Michalke et al., 2000 |

X, unidentified volatile metal(loids);
n.d., not detected;
*mediated by addition of octamethylcyclotetrasiloxane and the ionophores lasalocide and monensin.

Methylcobalamin [$CH_3Cob(III)$]-dependent methylation of As, Se, Sb, Te, Hg, and Bi has been reported for numerous anaerobic prokaryotes. In particular, autotrophic sulfate-reducing bacteria as well as methanoarchaea were suggested to be responsible for this process, as $CH_3Cob(III)$ and $CH_3Cob(III)$-dependent enzymes are integral parts of physiological pathways such as carbon fixation via the reductive acetyl-coenzyme A (CoA) pathway and methanogenesis. Hence, these organisms contain high concentrations of corrinoids. Nonenzymatic methylation of some metal(loid)s, like As and Hg, by $CH_3Cob(III)$ under reductive conditions was assumed by some researchers.

Figure 1:
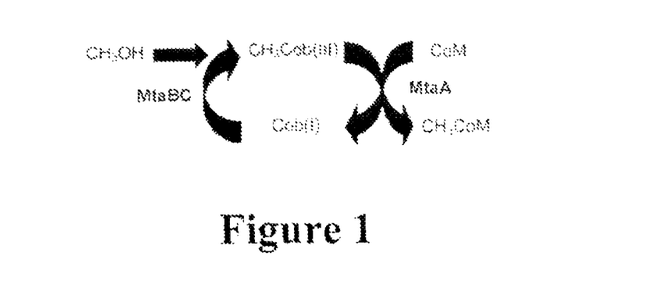
FIG. 1 shows CoM methylation in the methanol-utilizing methanogenic pathway of *M. mazei*.

In methanogenesis, the methyl group of $CH_3Cob(III)$ is transferred to 2-mercaptoethanesulfonate (CoM) in the penultimate step of methane formation, forming methylated CoM ($CH_3CoM$) and reduced cobalamin [Cob(I)] (18). In the methanol-utilizing methylotrophic pathway, this step is catalyzed by the methyltransferase MtaA (FIG. 1).

As researchers have shown the mechanism for the biomethylation of arsenic has been studied extensively with various fungi, bacteria, archaea, and mammals, including humans. As proposed by Challenger (1945), the biomethylation of selenium and tellurium follows the same mechanism as arsenic. Mercury biomethylation, on the other hand, has been studied in more detail because of poisonings by methylmercury compounds. Additionally the methylated antimony species, trimethylantimony, was detected as a biovolatilization product of antimony in the headspace of soil samples and of pure cultures of *Scopulariopsis brevicaulis*. The biomethylation of inorganic tin has also been reported, although research on organotin compounds has focused mainly on the fate of organotin species, which are used as biocide additives. These compounds are leached out in aquatic environments and undergo dealkylation and methylation. The methylated bismuth species, trimethylbismuth (TMBi), has been found in gases released from municipal waste deposits and sewage gases, but the origin of this compound is unclear.

Figure 2:
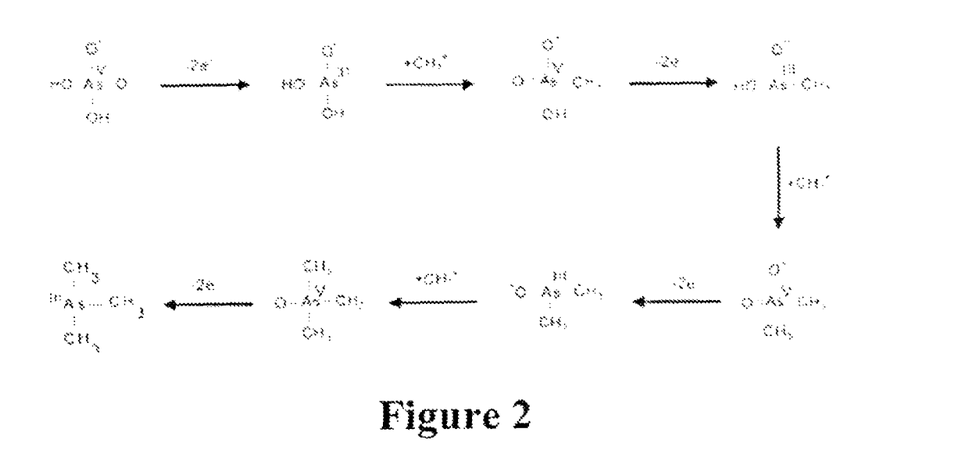
FIG. 2 shows a challenger mechanisms for biosynthesis or Arsenate.

Biomethylation of arsenic to trimethylarsine was confirmed in fungi by Frederick Challenger and his co-workers in 1933. FIG. 2 shows the stepwise path involving oxidative addition followed by the reductive elimination that was later proposed for enzymatically catalyzed methylation. Challenger suggested that "active methionine," later identified as S-adenosylmethionine (SAM), was the methyl group donor. Notably, the Challenger pathway is analogous to the uncatalyzed oxidative addition reaction known as the Meyer reaction that is used to prepare MMA(V) from arsenite and methyl halide. The Challenger pathway can be fully modeled by using the trimethylsulfonium ion as methyl donor and sulfur dioxide as the reducing agent.

Challenger's pathway makes clear predictions about the reaction in which a methyl group is transferred to an arsenic atom, about the charge on the methyl group, and about the oxidation state of the arsenic atom during and after the transfer. The pathway is usually written in terms of oxy-species, but it can be reasonably assured that the As—S bonding plays a major role because of the kinetic stability of the As—S bond to hydrolysis (one of the sources of the well-known affinity of As for S). Electrons for reduction of the methylarsenic(V) species to methylarsenic(III) probably come from oxidation of two thiols to a disulfide as in the real or notional reductive elimination reaction suggested for model systems: $R3As(SR')2 \rightarrow R3As: + R'S—SR'$ 0.16 In enzymatically catalyzed reactions, physiological dithiols such as thioredoxin or glutaredoxin which are reversibly oxidized likely provide these electrons.

Figure 3:
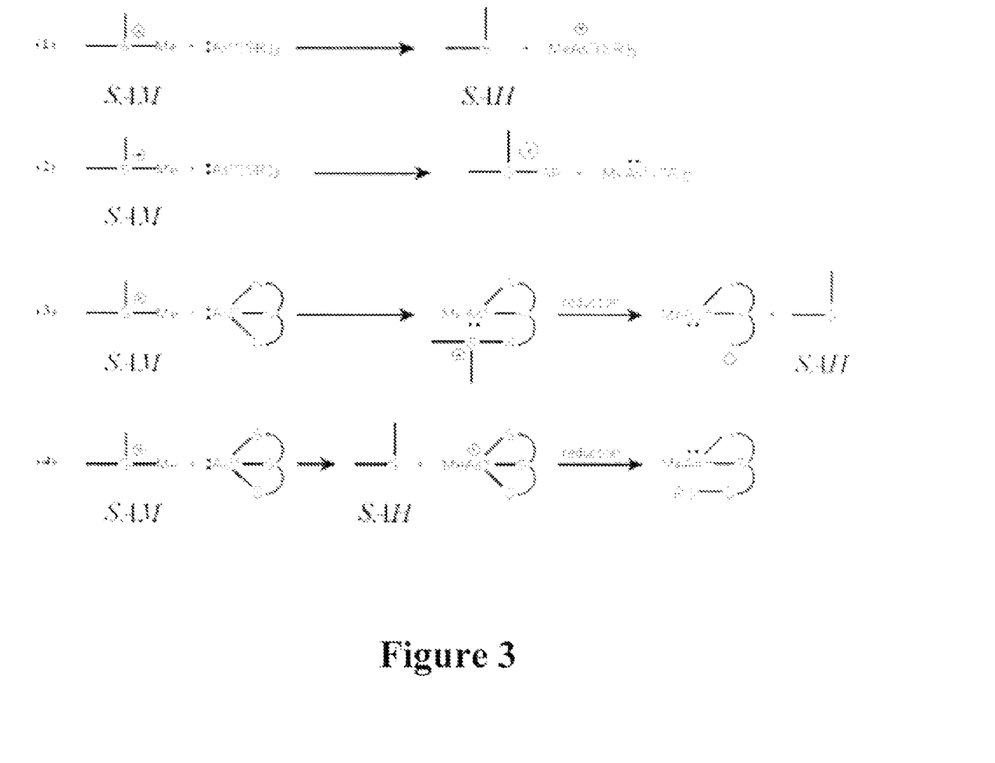
FIG. 3 shows equations describing the biological methylation of arsenic.

FIG. 3 summarizes postulated steps in the methylation of arsenic by the Challenger and alternative pathways. Equation 1 in FIG. 3 shows a variant form of Challenger's pathway in which the As(III) reactant is written as a tris-thiol derivative such as arsenic tris-glutathione. Here, transfer of the electrophile $CH_3+$ from SAM to an As(III) atom yields Sadenosylhomocysteine (SAH), a neutral species, and a methylated arsenical containing an As(V) atom. This is a chemically plausible reaction scheme because there is no possibility of an unfavorable electrostatic interaction between the positive leaving group and the uncharged SAH.

"Reductive methylation", is the heart of an alternative pathway proposed by other researchers. They suggest that the oxidative methylation and reductive elimination reactions of the Challenger pathway occur simultaneously so that the "real" reaction product is an arsenic(III) species. Therefore, this reaction scheme would significantly reduce the nucleophilicity of the lone electron pair on arsenic and inhibit the reaction.

Other reaction schemes have been suggested based on evidence from studies that used purified arsenic methyltransferases. Two such proteins have been identified and their genes cloned. Arsenic (+3 oxidation state) methyltransferase (As3mt) catalyzes arsenic methylation in a wide range of higher organisms, and arsenic methyltransferase (ArsM) catalyzes these reactions in Archaea, some eukaryotes, and many prokaryotes.

Mercury is a naturally occurring element that is found in air, water and soil. It exists in several forms: elemental or metallic mercury, inorganic mercury compounds, and organic mercury compounds. In its elemental form or as inorganic salts, it is relatively less toxic. However, when mercury in these forms is discharged into natural waterways, it is converted into highly toxic and malicious methylmercury ion, $CH_3Hg^+$.

The methylation of mercury in water bodies is occurring due to the presence of methanogenic bacteria. Higher levels of methylmercury substances, such as methylmercury chloride are found in deep rather than shallow sediments, indicating that biomethylation largely occurs under anaerobic conditions. The conversion of mercury into its methylated form is fostered by the enrichment of water with organic impurities that permit the growth of methanogenic bacteria. Biomethylation proceeds most effectively in the pH range of 5.5-6.5.

The methylated mercury (MeHg) species monomethyl mercury (MMHg) and dimethylmercury (DMHg) are typically measured at much less than 0.5 pM in aquatic regions, yet MMHg is the form that accumulates in biota. In freshwater and coastal ecosystems the bulk of methylated mercury production is MMHg, thought to be mediated by anaerobic bacteria, particularly sulfatereducing bacteria (SRB), in the redox transition zones of the anoxic layers of the sediment and water column. By analogy, it is thus conceivable that Hg methylation in the open ocean may occur principally in anoxic or sub-oxic zones.

Monomethyl mercury ($CH_3Hg^+$, methylmercury, MeHg) is a potent neurotoxic compound. It is biomagnified in the food webs of aquatic systems, reaching high concentrations in carnivorous fish, thus posing a risk to human health. The production of MeHg has been linked to obligate anaerobic bacteria in the δ-Proteobacteria, including iron and sulfate-reducing bacteria (FeRB and SRB) that live in soil and sediments. Although mechanisms of Hg(II) methylation by methylating enzymes have been proposed, the mechanism of Hg(II) uptake by the bacteria has remained obscure. The dominant view is that cellular uptake occurs by passive diffusion of neutral Hg(II) complexes, particularly sulfide complexes, through external membranes, leading to accidental methylation of some of the intracellular Hg(II). However, this view is based on indirect data and modeling, as the precipitation of metal sulfides in the medium and the extensive Hg binding to the surface of the organisms have made it difficult to directly measure Hg(II) uptake in methylating bacteria.

Research on the biological mechanism of mercury methylation has been conducted on one strain of SRB, *Desulfovibrio desulfuricans* LS. A corrinoid-containing protein was identified as key to mercury methylation capacity in inhibition experiments. From $^{14}C$-labeling studies and enzyme activity experiments, researchers concluded that the corrinoid-containing protein responsible for mercury methylation in *D. desulfuricans* LS is involved in the acetyl-coenzyme A (CoA) pathway.

Figure 4:
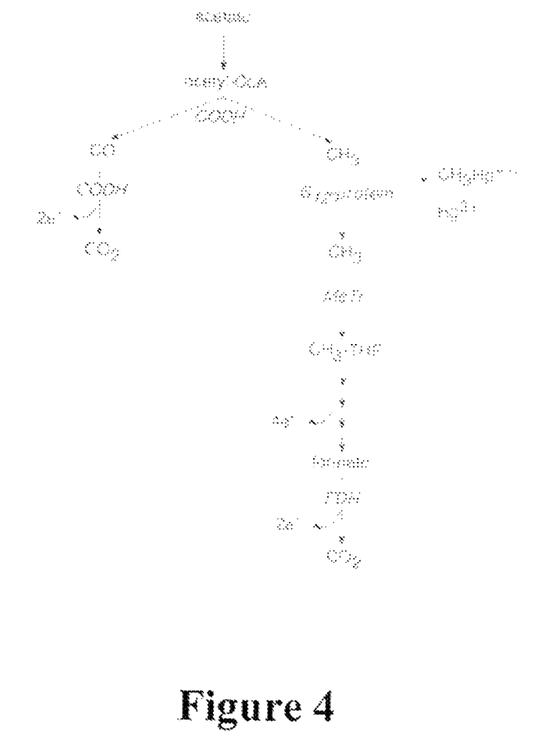
FIG. 4 shows an acetyl-CoA pathway as used for acetate oxidation.

The acetyl-CoA pathway (FIG. 4) is a carbon metabolism pathway that converts acetate into carbon dioxide (and vice versa), through the breakdown of acetate into carbon monoxide (CO) and a methyl moiety by carbon monoxide dehydrogenase (CODH), and subsequent oxidation of both to $CO_2$. Prior research with *Moorella thermoacetica*, a non-Hg methylating acetogen, identified a corrinoid-containing protein in the pathway that donated a methyl group to CODH. Presumably, a similar corrinoid protein is involved in the acetyl-CoA pathway in SRB.

SUMMARY OF THE DISCLOSURE

A method for inhibiting the methane production, and subsequently constraining the biomethylation reaction process of the heavy metals, under induced or naturally occurring anaerobic conditions in aqueous or soil media, is disclosed.

The disclosed method demonstrates the effective use of naturally-occurring statins to assess the methane produced from the enclosed anaerobic digester systems. The naturally-occurring statins, such as Lovastatin ($C_{24}H_{36}O_5$) can be obtained by the use of the commercially available red yeast rice extract. The aforementioned composition blocks the 3-hydroxy-3-ethylglutaryl coenzyme A (HMG-CoA) reductase, and the 8-hydroxy-5-deazaflavin (coenzyme $F_{420}$) in the methane production pathway, due to the presence of the statin.

DETAILED DESCRIPTION

Biological methanogenesis widely occurs in natural environments including soils, water, deep sea and digestive systems of some animals and plays an important role in global carbon cycling. Methane producing microorganisms, mainly methanogenic Archaea, which obtain energy for growth by converting a limited number of substrates to methane, are common in anaerobic environments where organic matter undergoes decomposition. The main precursor for methane production by methanogens is often acetate, which is one of the most abundant products from anaerobic digestion of organic matter via bacterial catabolism. Two mechanisms for methane generation from acetate by methanogens have been known, such as an aceticlastic reaction and a two-step process in which acetate is first oxidized to $H_2$ and $CO_2$, followed by their subsequent conversion to methane by methanogens. In the latter process, although some methanogens, such as Methanosarcinaceae, are capable of independently oxidizing acetate by themselves, various syntrophic bacteria are also involved in multistep processes such as acetogenic fermentation, syntrophic acetate oxidation, and hydrogenotrophic methane production.

The methanogenic Archaea (methanogens) occupy a variety of anaerobic habitats, where they play a role in the conversion of hydrogen and other intermediates to methane. The hydrogenotrophic methanogens use hydrogen to reduce $CO_2$ to methane. In addition, some hydrogenotrophs use formate, and a few substitute certain low-molecular-weight alcohols for hydrogen.

The deazaflavin $F_{420}$ is a common coenzyme of methanogenesis. The reduction of $CO_2$ to methane commonly includes reduced $F_{420}$ ($F_{420}H_2$), since it is the sole electron donor for the step that reduces methylenetetrahydromethanopterin (methylene-$H_4$MPT). In addition, $F_{420}H_2$ is the electron donor for $F_{420}H_2$-dependent methylenetetrahydromethanopterin dehydrogenase (Mtd), one of two enzymes that reduce methenyl-H4MPT. The other enzyme, $H_2$-dependent methylenetetrahydromethanopterin dehydrogenase (Hmd), uses $H_2$ directly. mRNA abundance for Mtd increased markedly under hydrogen-limited growth conditions, suggesting that Mtd may be useful when $H_2$ is limiting.

Figure 5:
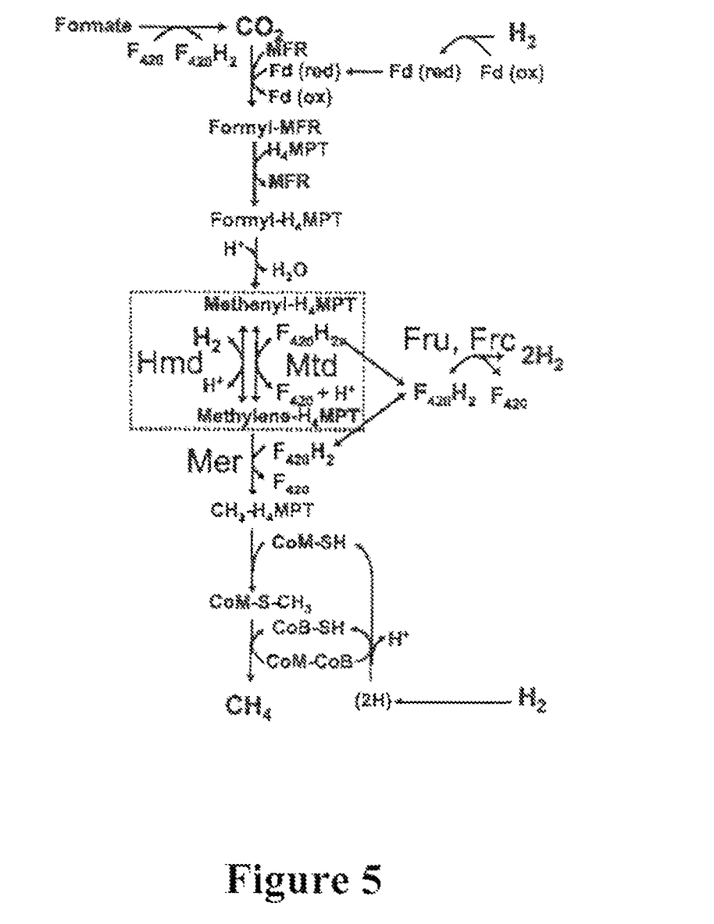
FIG. 5 shows a hydrogenotrophic methanogenic pathway.

The $F_{420}$-reducing hydrogenases (Fru and Frc) reduce $F_{420}$ with $H_2$. However, an alternative route for this process has been proposed. In *Methanothermobacter marburgensis* the specific activity of $F_{420}$-reducing hydrogenase, a Ni—Fe hydrogenase, decreased 20-fold under nickel-limited growth conditions. In contrast, the specific activities of Hmd and Mtd, neither of which requires nickel for activity, increased six- and fourfold, respectively. These observations led to the proposal that under nickel-limited conditions, $F_{420}$ may be reduced by the concerted action of Hmd and Mtd, the former working in the forward direction (with respect to the methanogenic pathway) and the latter in the reverse direction. This pathway is presented in FIG. 5.

Sharma et al. (2011) determined a 3D model structure of the $F_{420}$-dependent NADP oxidoreductase enzyme from *M. smithii*. Based on their protein model, they detected that these residues are making a ligand binding site pocket, and they found that ligand $F_{420}$ binds at the protein cavity. The inhibitor compounds lovastatin and compactin (mevastatin) show more affinity for the model protein as compare to the natural ligand $F_{420}$. They share the same cavity as by $F_{420}$ and surround by similar residues. Therefore, the inhibitor compounds lovastatin and compactin (mevastatin) were very effective in blocking the activity site for methane production since the enzyme was unable to bind with the substrate, resulting in decreased methane production.

The acetyl coenzyme A (CoA) pathway commonly referred to as the Wood-Ljungdahl pathway or the reductive acetyl-CoA pathway is one of the major metabolic pathways utilized by methanogenic bacteria. This specific pathway is characterized by the use of hydrogen as an electron donor and carbon dioxide as an electron acceptor to produce acetyl-CoA as the final product. The acetyl-CoA pathway begins with the reduction of a carbon dioxide to carbon monoxide. The other carbon dioxide is reduced to a carbonyl group. The two major enzymes involved in these processes are carbon monoxide dehydrogenase and acetyl CoA synthase complex. The carbon dioxide that is reduced to a carbonyl group, via the carbon monoxide dehydrogenase, is combined with the methyl group to form acetyl-CoA. The acetyl-CoA synthase complex is responsible for this reaction. The 3-hydroxy-3-methylglutaryl coenzyme A (HMG-CoA) reductase, is an important enzyme in methane production in *Methanobrevibactor* strains, since Archaea are bacteria known to possess biosynthetic HMG-CoA reductase.

Lovastatin is a secondary product of idiophase (secondary phase) of growth of fungi and is an inhibitor of enzyme 3-hydroxy-3-ethylglutaryl coenzyme A (HMG-CoA) reductase, a key enzyme also in cholesterol production pathway in humans. There is a similarity between cholesterol formation in human and cell membrane formation in the Archaea (methanogens) as the lipid side of phospholipids in the cell membrane of Archaea isoprenoid chains. Isoprenoid formation is an intermediate step of cholesterol production pathway (Mevalonate pathway) and HMG-CoA reductase is also a key enzyme for its production. Therefore, as an inhibitor of HMG-CoA reductase, lovastatin suppresses isoprenoid production and thus cholesterol synthesis and methane formation in the Archaea.

Wolin and Miller (2005) showed that lovastatin significantly reduced growth and activity of pure methanogenic bacteria without any negative effect on cellulolytic bacteria. Further studies have shown that red yeast rice can successfully inhibit the key enzyme HMG-CoA reductase, resulting in the inhibition of methanogenic activity. Miller and Wolin (2001) also used Lovastatin to inhibit the formation of the key precursor mevalonate. Mevalonate is formed by reduction of HMG-CoA. Based on their results they found that lovastatin inhibited the growth of *Methanobrevibacter* and subsequently the methane production. In fact 4 nmol/ml of culture medium resulted in 50% inhibition of growth and concentrations 10 nmol/ml of culture medium completely inhibited growth. Methane formation was also significantly inhibited. At the same time the populations of the non-methanogens were not affected.

The use of red yeast rice under naturally existing or technically induced reducing anaerobic conditions inhibits the biomethylation of heavy metals by methanogens. As a result, the established reaction mechanisms for immobilization of various heavy metals under reducing conditions will be more effectively undertaken (Table 2). Moreover, the overall toxicity of the site is not increased via the generation of methylmetal(loids) as a consequence of the treatment process.

TABLE 2

Overview of Heavy Metal Immobilization Reactions during Anaerobic Conditions

| Dissolved Metal | STABILIZATION / IMMOBILIZATION MECHANISMS | REFERENCE |
|---|---|---|
| As (III, V) | Reductive precipitation with oxidized iron minerals. Precipitation as As sulfide and mixed Fe—As sulfide. | Blowes et al, 2000; Manning et al., 2002; Craw et al., 2003 |
| Cr(VI), Mo(VI), Se(IV, VI), U(VI) | Reductive precipitation with oxidized iron minerals adsorption to iron oxides. | Blowes et al., 2000;, 8 |
| $Me^{2+}$ (Cu, Zn, Pb, Cd, Ni) | Organic carbon source stimulates heterotrophic microbial sulfate reduction to sulfide and metal cations precipitate as sulfides. Also strong adsorption to iron corrosion products (e.g. iron oxides and oxyhydroxides). | Blowes et al., 2000; Dzombak and Morel, 1990 |
| $Hg^{2+}$ | Mercury is commonly converted by microorganisms to monomethyl mercury ($CH_3Hg$) and dimethyl mercury [$(CH_3)_2Hg$)]. If not organically complexed, mercury can reductively precipitate as mercury sulfide. Also strong adsorption to iron corrosion products (e.g.; iron oxides and oxyhydroxides). | Blowes et al., 2000; Dzombak and Morel, 1990 |

For example, metal cations such as Cu, Zn, Hg, Pb, Cd, and Ni will precipitate as metal sulfides following microbial mediated reduction of sulfate present in the groundwater. The presence of sulfate in the subsurface as well as the additional introduction of sulfate as a remedial substance along with the biodegradation of carbon sources will stimulate the sulfate-reducing bacteria and the process could be represented by the following equations:

$$2CH_2O_{(s)} + SO_4^{2-} + 2H^+_{(aq)} \rightarrow H_2S + 2CO_{2(aq)} + H_2O$$

$$Me^{2+}_{(aq)} + H_2S_{(aq)} \rightarrow MeS_{(s)} + 2H^+_{(aq)}$$

where $CH_2O$ represents organic carbon and $Me^{2+}$ represents a divalent metal cation.

EXAMPLES

Two bench scale studies were performed to test the effectiveness of the methane inhibitor red yeast rice (RYR).

Purpose

The purpose of the two laboratory studies was to evaluate the effectiveness of Methane Inhibitor Red Yeast Rice (MIRYR), a composition developed by the inventors herein. The product was designed to inhibit methane production in environments where methanogens are established and active.

Materials and Methods

Laboratory Study 1

Two anaerobic reactors were utilized, a Control and a Test reactor. The two reactors were seeded with biomass treating expired dietary supplement, which contained an active methanogenic population. The reactors were fed once per week, and were operated as anaerobic sequencing batch reactors.

During the first week of startup, the reactors contained only the methanogenic culture, without soil. After one week, silty sand was added, resulting in a slurry having a solids concentration of 20% by weight. The reactors were operated for another week with the silty sand, to ensure that the sand did not affect methanogenic activity. The bioreactors were 2.5 L in volume, containing 2 L of slurry. The reactors were airtight and were especially designed for anaerobic reactions. The reactors were maintained at laboratory temperature 22° C.-24° C. The reactors were operated by feeding with dietary supplement once a week. The target initial chemical oxidation demand ("COD") concentration after feeding was 2000 mg/L. Throughout the week, the volume of biogas produced was measured as follows. A syringe was inserted periodically into a septum-filled port in the top of the reactor to collect a gas sample for methane content. The methane content of the biogas samples was then quantified by injecting into a gas chromatograph with a flame ionization detector (GC-FID). The reactors had dedicated probes to measure pH and oxidation reduction potential ("ORP"). After each cycle (i.e., before feeding), a probe was inserted into the reactor to measure total dissolved solids ("TDS"), and a sample was collected to measure COD. The mixer was turned off during sampling and feeding to minimize the introduction of oxygen into the reactor contents.

The Test reactor was initially dosed with a 40 g/L concentration of Methane Inhibitor RYR (MIRYR). One week later the Control was dosed with 20 mg/L MIRYR.

Laboratory Study 2

Two test aliquots were prepared under a nitrogen atmosphere in a glove box as follows:
1. A 240 mL amber glass screw-cap septum bottle was filled with 100 g of dry soil (~70 mL).
2. Deoxygenated deionized water was slowly added to the soil to saturate the soil; an additional 40 mL of water was then added to the soil.
3. Manure slurry was added to yield a 1 weight percent manure dose to the soil.

Once the bottle was sealed it was removed from the glove box. The soil was kept in the dark (by wrapping with foil) at room temperature (~22° C.). A needle connected to a polyethylene tube was pushed through the bottle septum and the tube outlet was placed in an inverted graduated cylinder in a water bath. The gas generation rate was recorded as the water was displaced over a period of 10 days.

The methane reduction trial included two sample formulations, with and without MIRYR, for a total of 4 samples. The bottles were sampled 0.5, 1.5, 5, 12, and 19 days following the sample preparation.

Results

Laboratory Study 1

The first two weeks of the studies were the Startup Period, and the second two weeks were the Test Period. The Startup Period established the methanogenic population in the two reactors. During the first week of startup, the reactors were operated without the silty sand, and the second week they were operated with the silty sand (20% by weight). The Test Period started with the dosing of the Test reactor with MIRYR (40 g/L). During the first week of the Test Period the Control was maintained as a proper control, with no MIRYR added. Because the 40 mg/L dose of MIRYR reduced methane production in the Test reactor, it was decided to dose the Control reactor with 20 g/L of MIRYR during the second week of the Test Period. The Test Period lasted 17 days.

Table 3 lists the volume of biogas production, pH values, and the concentrations of COD, ORP, and TDS measured in the Control and Test reactors during the studies. The volume of biogas produced each feed cycle (i.e., each week) in the reactors ranged between 72-82 mL. It is notable that the volume of gas was not affected by the introduction of silty sand during week 2 of the Startup period. The addition of 40 mg/L of MIRYR to the test in the first week of the Test period and the addition of 20 mg/L of MIRYR during the second week of the Test period did not appreciably impact biogas volume in the reactors. The COD measurements after each sequencing batch reactor cycle ranged from 56 to 108 mg/L. The reactors were fed 2000 mg/L each cycle, so the COD concentrations in Table 3 demonstrate that the COD was consumed by the anaerobic culture. Values of pH ranged between 6.1 and 6.4. Values of ORP were all close to −300 mV, which is typical of methanogenic conditions. The TDS in the reactors ranged from approximately 1200 to 1250 mg/L.

TABLE 3

A list of the biogas volume, pH values, and concentrations of COD, ORP, and TDS in the Control and the Test reactors throughout the studies.

| Period | Gas Vol. (mL) | COD (mg/L) | pH | ORP (mV) | TDS (mg/L) |
|---|---|---|---|---|---|
| CONTROL | | | | | |
| Startup-Week 1 | 81 | 56 | 6.4 | −302 | 1213 |
| Startup-Week 2 | 72 | 91 | 6.3 | −306 | 1241 |
| Test- Week 1 | 75 | 61 | 6.2 | −289 | 1258 |
| Test- Week 2 | 73 | 108 | 6.3 | −296 | 1220 |
| TEST | | | | | |
| Startup-Week 1 | 79 | 72 | 6.2 | −285 | 1244 |
| Startup-Week 2 | 75 | 83 | 6.2 | −298 | 1265 |
| Test- Week 1 | 82 | 62 | 6.1 | −306 | 1263 |
| Test- Week 2 | 72 | 97 | 6.4 | −287 | 1247 |

Figure 6:
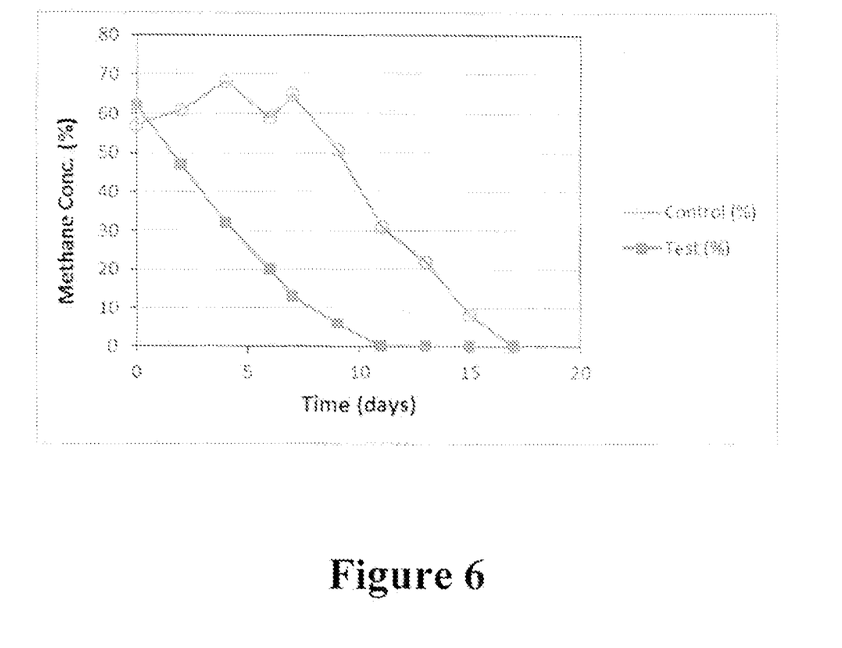
FIG. 6 shows a graph of the methane concentrations listed in Table 4.

Table 4 lists the methane content measured in the biogas generated in the reactors during the 17-day study period. FIG. 6 shows a graph of the methane concentrations listed in Table 4. During the Startup Period, methane concentrations varied from approximately 55% to 70%, which indicates an active methanogenic culture. The MIRYR dose of 40 mg/L in the Test reactor reduced the methane content of biogas from 62% to below detection (0.05%) after 11 days. The methane concentration remained below detect in the Test reactor until day 17, when the reactors were dismantled. The MIRYR dose of 20 mg/L in the Control reactor on day 7 reduced the methane content of biogas from 65% to below detection (0.05%) by day 17 (i.e., after 10 days). During the Test period, the volume of biogas produced in the Test and Control reactors did not change appreciably (Table 4) only the methane concentration of the biogas was changed.

TABLE 4

A list of the methane concentrations (%) measured in the biogas during the Test Period (i.e., after dosing with methane inhibitor).

| Activity | Time (days) | Control (%) | Test (%) |
|---|---|---|---|
| dosed Test (40 mg/L) | 0 | 57 | 62 |
| | 2 | 61 | 47 |
| | 4 | 68 | 32 |
| | 6 | 59 | 20 |
| dosed Control (20 mg/L) | 7 | 65 | 13 |
| | 9 | 51 | 6 |
| | 11 | 31 | 0 |
| | 13 | 22 | 0 |
| | 15 | 8 | 0 |
| | 17 | 0 | 0 |

It is understood that the invention is not limited to the disclosed embodiments and examples, but is intended to cover various modifications and equivalent arrangements included within the spirit and scope of the appended claims.

Laboratory Study 2

Table 4 lists the methane content measured in the biogas generated in the reactors during the 19-day study period. The first soil formulation (SF1) that contains 20% of the MIRYR (approximately 40 mg/L in solution) showed great effectiveness in inhibiting the methane production by 96% during the 19-day sampling interval. Similarly at the same time frame the second soil formulation (SF2) resulted into a 25% decrease in methane production.

TABLE 5

A list of the methane concentrations (%) measured in the biogas of the seven sample formulations during the Test Period.

| Time (days) | SF1 (no MIRYR) | SF1 (with 20% MIRYR) | SF2 (no MIRYR) | SF2 (with 10% MIRYR) |
|---|---|---|---|---|
| 0.5 | 1.0 | 0.0 | 1.0 | 0.0 |
| 1.5 | 1.0 | 2.0 | 7.0 | 8.0 |
| 5 | 5.0 | 5.0 | 0.0 | 5.0 |
| 12 | 1.39 | 0.79 | 0.94 | 0.86 |
| 19 | 3,217 | 140 | 2,685 | 2,023 |

SF: Sample Formulation

The above examples show that the disclosed embodiment is able to reduce methane and therefore results in the constrainment of a biomethylation process of heavy metals present in a contaminated media. A person skilled in the art will be able to perform simple testing using the disclosed embodiments to determine an effective amount for reducing methane constraining the biomethylation process for specific metals, such as groups IV, V and VI in the periodic table, as well as groups IB, IIB, IIIB, IVB, VB, VIB and VIIB in the periodic table. Further, a person skilled in the art will be able to determine an effective amount for use in an environmental medium, including soil or groundwater.

Once again, it is understood that the invention is not limited to the disclosed embodiments and examples, but is intended to cover various modifications and equivalent arrangements included within the spirit and scope of the appended claims.

What is claimed is:

1. A method for inhibiting methane production under induced or naturally occurring reducing conditions in a contaminated media, the method comprising
contacting the contaminated media with a composition comprising red yeast rice, wherein an amount of the composition is sufficient to cause inhibition of methane production of methanogens within the contaminated media by blocking 8-hydroxy-5-deazaflavin (coenzyme F420) in a methane production pathway, and wherein the inhibition of the methane production results in constrainment of a biomethylation process of heavy metals within the contaminated media.

2. The method of claim 1, wherein the contaminated media is an environmental medium.

3. The method of claim 2, wherein the environmental medium is soil or groundwater.

4. The method of claim 1, wherein the heavy metals that are subject to the constrainment of the biomethylation process include heavy metals from Groups IV, V and VI in the periodic table.

5. The method of claim 1, wherein the heavy metals that are subject to the constrainment of the biomethylation process include transition metals from Groups IB, IIB, IIIB, IVB, VB, VIB, VIIB and VIIB in the periodic table.

6. The method of claim 1, wherein the composition is further to inhibit the methane production of the methanogens within the contaminated media by blocking 3 hydroxy-3-ethylglutaryl coenzyme A (HMG-CoA) reductase in the methane production pathway.

7. The method of claim 1, wherein the composition includes a naturally-occurring statin.

8. The method of claim 7, wherein the naturally-occurring statin is lovastatin.

9. The method of claim 8, wherein the red yeast rice provides the lovastatin.

10. The method of claim 1, wherein the inhibition of methane production results in inhibition of methylmetal(loid) production that is part of the biomethylation process of the heavy metals.

11. A method for constraining biomethylation of heavy metals within a contaminated media, the method comprising
    contacting the contaminated media with a composition comprising red yeast rice to inhibit methane production of methanogens within the contaminated media by blocking 8-hydroxy-5-deazaflavin (coenzyme F420) in a methane production pathway, wherein methane within the contaminated media leads to the biomethylation of the heavy metals so inhibiting the methane production constrains the biomethylation.

12. The method of claim 11, wherein the contaminated media is soil or groundwater.

13. The method of claim 11, wherein the heavy metals include Group IV, V and VI metals from the periodic table.

14. The method of claim 11, wherein the heavy metals include transition metals from Groups IB, IIB, IIIB, IVB, VB, VIB, VIIB and VIIB in the periodic table.

15. The method of claim 11, wherein the composition is further to inhibit the methane production of the methanogens within the contaminated media by blocking 3-hydroxy-3-ethylglutaryl coenzyme A (HMG-CoA) reductase in the methane production pathway.

16. The method of claim 11, wherein the red yeast rice provides a naturally-occurring statin.

17. The method of claim 11, wherein the red yeast rice provides a lovastatin.

18. The method of claim 11, wherein the inhibition of the methane production of the methanogens inhibits methylmetal(loid) production that is part of the biomethylation process of the heavy metals.

19. A method for inhibiting production of methylmetal(loids) from heavy metals within a contaminated media, the method comprising
    providing a composition including red yeast rice to the contaminated media in order to inhibit methane production of methanogens within the contaminated media by blocking 8-hydroxy-5-deazaflavin (coenzyme F420) in a methane production pathway, wherein methane and the heavy metals within the contaminated media interact to produce the methylmetal(loids), and wherein the inhibiting of the methane production of the methanogens within the contaminated media inhibits the methylmetal(loids) production.

20. The method of claim 19, wherein the contaminated media is soil or groundwater.

* * * * *

UNITED STATES PATENT AND TRADEMARK OFFICE
CERTIFICATE OF CORRECTION

PATENT NO. : 9,637,731 B2
APPLICATION NO. : 14/532689
DATED : May 2, 2017
INVENTOR(S) : Michael Scalzi and Antonis Karachalios It is certified that error appears in the above-identified patent and that said Letters Patent is hereby corrected as shown below:

Delete drawing sheets 1-5 and replace with attached drawing sheets 1-5.

Signed and Sealed this
Third Day of October, 2017

Joseph Matal
*Performing the Functions and Duties of the*
*Under Secretary of Commerce for Intellectual Property and*
*Director of the United States Patent and Trademark Office*

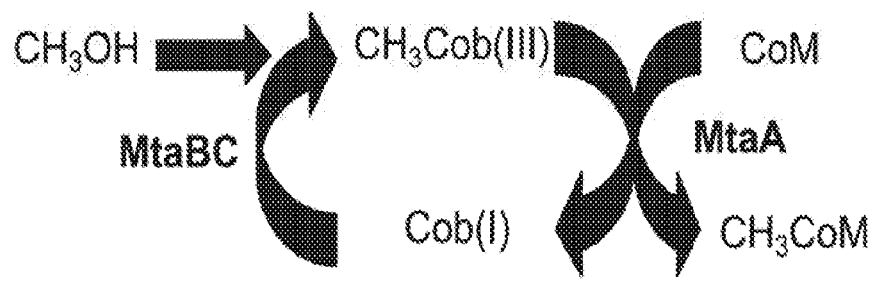
FIG. 1
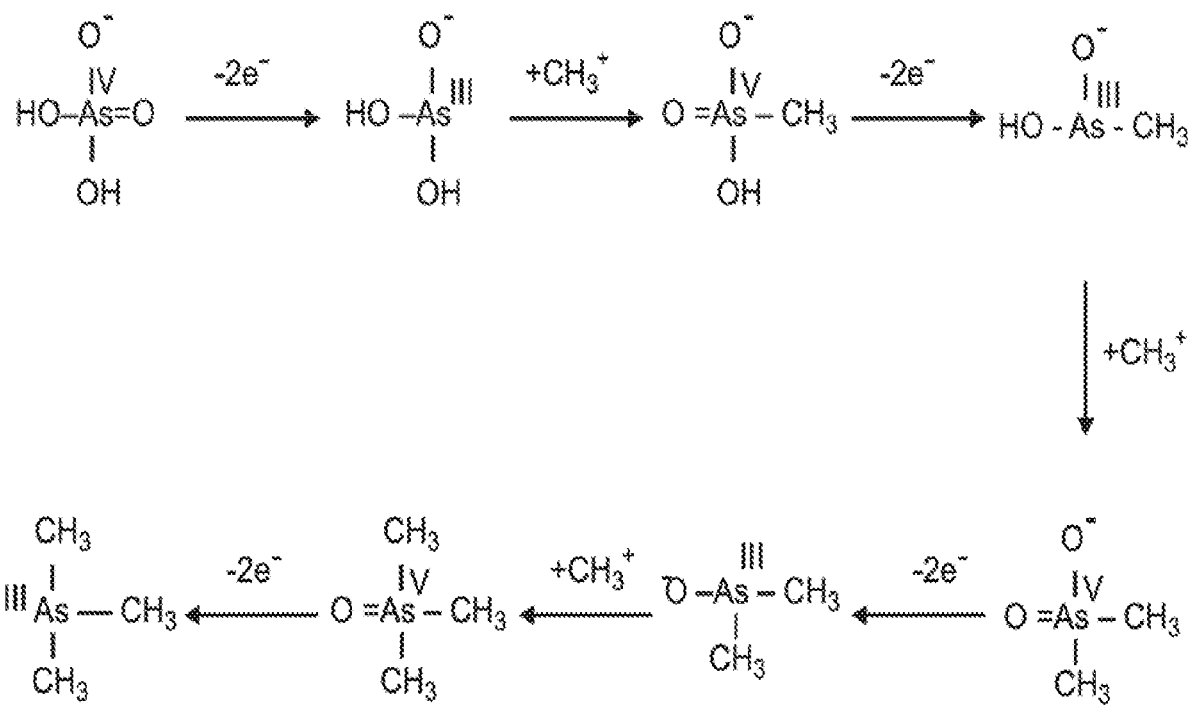
FIG. 2

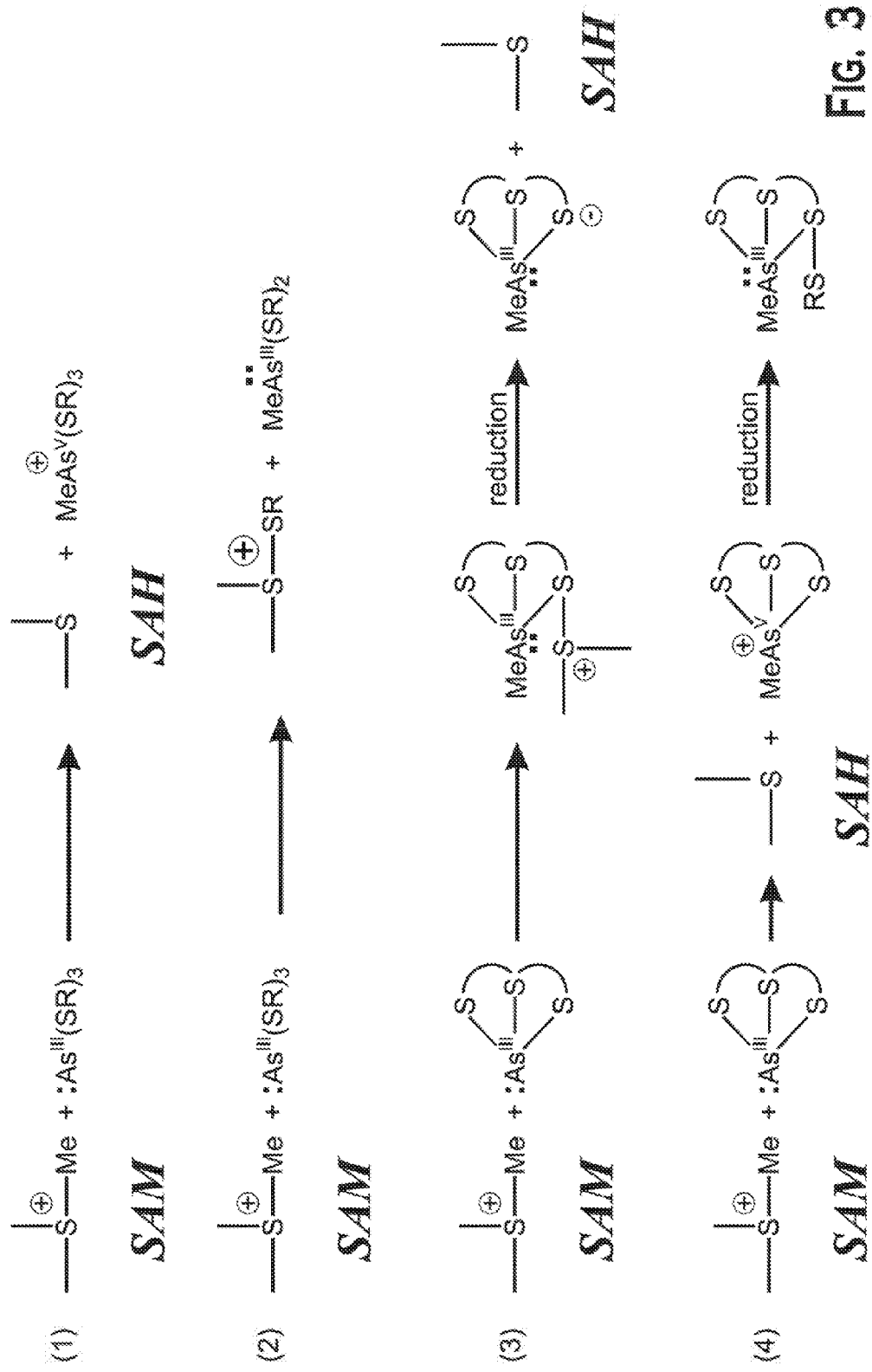
Fig. 3